United States Patent [19]

Madsen et al.

[11] Patent Number: 4,843,866

[45] Date of Patent: Jul. 4, 1989

[54] ULTRASOUND PHANTOM

[75] Inventors: Ernest L. Madsen; James A. Zagzebski; Gary R. Frank, all of Madison, Wis.

[73] Assignee: Wisconsin Alumni Research Foundation, Madison, Wis.

[21] Appl. No.: 156,382

[22] Filed: Feb. 16, 1988

Related U.S. Application Data

[63] Continuation of Ser. No. 915,449, Oct. 6, 1986, abandoned.

[51] Int. Cl.⁴ ............................................. G01N 37/00
[52] U.S. Cl. ................................................... 73/1 DV
[58] Field of Search ................. 73/1 R, 1 DV; 367/13

[56] References Cited

U.S. PATENT DOCUMENTS

| | | | |
|---|---|---|---|
| 4,286,455 | 9/1981 | Ophir et al. | 73/1 DV |
| 4,331,021 | 5/1982 | Lopez et al. | 73/1 DV |
| 4,406,153 | 9/1983 | Ophir et al. | 73/1 DV |

FOREIGN PATENT DOCUMENTS 2814336  5/1979  Spain.

OTHER PUBLICATIONS

Goldstein et al., (1983), "Particle Image-Resolution Test Object", *J. Ultrasound Med.*, 2, 195–209.

Goodsitt, M. M. (1982), *A Three Dimensional Model for Generating the Texture in B-Scan Ultrasound Images*, PhD Thesis, University of Wisconsin, Madison, Wis., pp. i–iii, 203–216.

Goodsitt et al. (1983), "A Three Dimensional Model for Generating the Texture in B-Scan Ultrasound Images," *Ultrasonic Imaging*, 5 253–279.

Madsen et al. (1982), "Anthropomorphic Breast Phantoms for Assessing Ultrasonic Imaging System Performance and for Training Ultrasonographers: Part I," *J. Clin. Ultrasound*, 10, 67–75.

Madsen et al. (1982), "Anthropomorphic Breast Phantoms for Assessing Ultrasonic Imaging System Performance and for Training Ultrasonographers: Part II," *J. Clin. Ultrasound*, 10, 91–100.

Madsen et al. (1982), "An Anthropomorphic Ultrasound Breast Phantom Containing Intermediate-Sized Scatterers," *Ultrasound in Med. and Biol.*, 8, 381–392.

Madsen et al. (1984), "Method of Data Reduction for Accurate Determination of Acoustic Backscatter Coefficients," *J. Acoust. Soc. Am.*, 76, 913–923.

Smith, S. W. and H. Lopez (1982), "A Contrast-Detail Analysis of Diagnostic Ultrasound Imaging," *Med. Phys.*, 9, 4–12.

Smith et al. (1985), "Frequency Independent Ultrasound Contrast-Detail Analysis," *Ultrasound in Med. & Biol.*, 11, No. 3, 467–477.

Spitzer, B. M. et al. (1979), "Evaluation of Ultrasonic Array Image Quality," *Med. Phys.*, 6, 350.

Ultrasound Phantoms, ATS Laboratories, Sep. 1981.

*Primary Examiner*—Stewart J. Levy
*Assistant Examiner*—Robert R. Raevis
*Attorney, Agent, or Firm*—Lathrop & Clark

[57] ABSTRACT

An ultrasound phantom for use with an ultrasound scanner. The ultrasound phantom includes a container having a bottom and walls, margins of the walls remote from the bottom defining a window, which is closed by an ultrasound-transmitting window cover. A phantom body is contained within the container and includes a matrix made of a matrix material exhibiting a matrix ultrasonic speed, specific gravity, attenuation coefficient, and backscatter coefficient. The phantom body further includes a multiplicity of scattering particles spaced sufficiently close to each other that the scanner is incapable of resolving individual scattering particles and testing spheres having a testing sphere ultrasonic speed, specific gravity, attenuation coefficient, and backscatter coefficient, at least one of which is different from the corresponding matrix ultrasonic speed, specific gravity, attenuation coefficient, and backscatter coefficient. The testing spheres are located within the phantom body in a random array.

9 Claims, 4 Drawing Sheets

ULTRASOUND PHANTOM

This is a continuation, of application Ser. No. 915,449, filed Oct. 6, 1986 now abandoned.

TECHNICAL FIELD

The present invention relates to phantoms for testing diagnostic equipment and, in particular, to phantoms for testing the resolution capabilities of ultrasound scanners. "Resolution" is used herein to mean the capability of distinguishing an object from adjacent materials. Thus, an object must be "resolved" to be detected by an ultrasound scanner. "Ultrasound scanner" refers collectively to the scanning head and intercooperating mechanical and electronic components of such scanners, including a signal detection apparatus. Typically the signal detection apparatus includes a monitor displaying a visual image. To be "resolved" when only such a monitor is in use, an object must be detectable by an examination of such an image.

BACKGROUND OF ART

Those skilled in the art are aware of a variety of types of phantoms used to determine the resolution abilities of ultrasound scanners. Most of them involve phantoms containing objects to be detected. For example, one type contains metal or plastic fibers, arranged either individually or in pairs, oriented perpendicular to the scanning plane. An ultrasound scanner is tested by its ability to detect the fibers at all and also by a determination of the least separation between fibers such that they can still be resolved.

S. W. Smith and H. Lopez (1982), "A contrast-detail analysis of diagnostic ultrasound imaging," *Med. Phys.*, 9, 4–12, and S. W. Smith, H. Lopez, and W.J. Bodine, Jr. (1985), "Frequency independent ultrasound contrast-detail analysis," *Ultrasound in Med. and Biol.*, 11, 467–477, describe phantoms consisting of a block of gelatin containing eight long, thin cones or, alternatively, stepped cylinders of gelatin. Both the block of gelatin and the cones within it contain plastic beads or particles that function as ultrasound scatterers. Each cone or stepped cylinder contains such scatterers of a different size and/or concentration relative to the scatterers of the background material so that the scattering level of the background material is different from that of each cone or stepped cylinder. The cones or stepped cylinders extend in a plane held at right angles to the scanning plane, so that the size of the portion of a cone or cylinder within any given scanning slice can be varied from a small size near the tip of the cone or smallest step in the cylinder to a large size near the base of the cone or the largest step in the cylinder.

No attempt is made in the Smith phantoms to approximate the shape of the small lesions commonly being searched for in clinical applications of ultrasound scanning. As a consequence, neither the effect of the width of the slice being scanned nor the effect of the fact that an object to be resolved occupies only a part of the slice being scanned is dealt with. The use of only one cone of any given backscatter coefficient leads to other limitations. For example, statistical fluctuations of the "speckle" or "texture" patterns in ultrasound scanners can easily lead to situations in which a particular simulated lesion is overlooked (a false negative) or, on the other hand, a simulated lesion is thought to have been detected when in fact what is seen is an artifact of the machine (a false positive). The use of only a single object of a given backscatter coefficient increases the opportunities for false negatives. Thus, if only one test object is available to be detected and it is missed because of such statistical fluctuations in speckle or texture patterns, a statistical event may have effectively masked the actual ability of the scanner being tested to resolve such a test object. At the least, multiple scanning of the phantom would be necessary to avoid this source of error. False positives are rendered more likely when the location and number of objects to be resolved are known to the person testing the scanner so that random fluctuations are easier to erroneously identify as a resolved image. Certain terms relating to ultrasound, such as the terms "backscatter coefficient" (used above) and "attenuation coefficient" (see below), are well known to those skilled in the art and are used herein with the same meanings as are assigned to them in Madsen et al. (1984), "Method of data reduction for accurate determination of acoustic backscatter coefficients," *J. Acoust. Soc. Am.*, 76, 913–923.

A different approach to that of the Smith phantoms is seen in the phantom reported by A. Goldstein and W. Clayman (1983), "Particle image-resolution test object," *J. Ultrasound Med.*, 2, 195–209. The *Goldstein et al.* phantom employs a spatially random distribution of very small ultrasound scatterers distributed within a gel. Significance is attached to variations in the texture pattern of an ultrasound image of the phantom as a function of depth, with the amount of blurring in the image utilized as a measurement of resolution capabilities. In contrast to the *Smith* phantoms, in the *Goldstein et al.* phantoms there are no macroscopic variations in scattering particle concentrations, and no attempt is made to visualize an object within the phantom that simulates the sort of object that is to be detected in medical application of the scanning equipment.

In a published abstract, B. M. Spitzer, P. L. Carson, and A. L. Scherzinger (1979), "Evaluation of ultrasonic array image quality," *Med. Phys.*, 6, 350, stated that a "series of test objects consisting of cylindrical and spherical inclusions of non-scattering material in a polymer with approximately liver equivalent scattering has been constructed. Visual determination of acoustic noise levels in the anechoic volumes appear to be a simple, sensitive indicator of clinical image quality on real time arrays." The sizes of the spherical inclusions are not given in the abstract, and the abstract contains no discussion of whether the test objects are useful as a means of testing the ability of a scanner to resolve objects.

The PhD thesis of Mitchell M. Goodsitt (1982), *A Three Dimensional Model for Generating the Texture in B-scan Ultrasound Images*, Department of Medical Physics, University of Wisconsin, Madison, Wis., includes a discussion of a phantom that essentially was a gel block containing two spheres embedded within the gel that differed from the gel only in scatter coefficient. Small particle scatterers were distributed throughout the gel, but the embedded spheres contained none of them. The larger of the embedded spheres was one half inch in diameter, and the smaller was one quarter inch. The resulting phantom differed from the phantoms of *Smith* in that the effects of slice width could be studied. However, the diameters of the spheres were so large that the spheres would not tax the resolving ability of any commercial ultrasound scanner then or currently in use for medical diagnostic purposes. *Goodsitt et al.*

(1983), "A three dimensional model for generating the texture in B-scan ultrasound images," *Ultrasonic Imaging*, 5, 253-279, is based on the Goodsitt thesis and does not extend beyond it.

Madsen et al. (1982), "Anthropormorphic breast phantoms for assessing ultrasonic imaging system performance and for training ultrasonographers, Parts I and II," *J. Clin. Ultrasound*, 10, 67-75 and 91-100, describe anthropormorphic breast phantoms that include spherical objects embedded within a gel breast shape, one of the objects having the scatter characteristics of a cyst, another having the scatter characteristics of a breast tumor, and so forth. Madsen et al. (1982), "An anthropormorphic ultrasound breast phantom containing intermediate-sized scatterers," *Ultrasound in Med. & Biol.*, 8, 381-392, also describe a breast phantom including spherical objects having scatter coefficients resembling cysts and tumor materials. As with the *Goodsitt* phantom, these anthropomorphic breast phantoms were not designed to facilitate or be useful in testing the limits of the resolving abilities of ultrasound scanners. The objects were too large, too few in number, and of known location.

BRIEF SUMMARY OF THE INVENTION

The present invention is summarized in that an ultrasound phantom includes a container having a bottom and walls, margins of the walls remote from the bottom defining a window, which is closed by an ultrasound transmitting window cover. The ultrasound phantom further includes a phantom body contained within the container. The phantom body includes a matrix made of a matrix material exhibiting a matrix ultrasonic speed, specific gravity, attenuation coefficient, and backscatter coefficient. The phantom body further includes a multiplicity of testing spheres having a testing sphere ultrasonic speed, specific gravity, attenuation coefficient, and backscatter coefficient, at least one of which is different from the corresponding matrix ultrasonic speed, specific gravity, attenuation coefficient, and backscatter coefficient. The testing spheres are located within the phantom body in a random array and in size are within an order of magnitude of the smallest object that can be resolved by the ultrasound scanner head. The phantom body includes scattering particles spaced sufficiently close to each other that the scanner is incapable of resolving individual scattering particles. As used herein, the "ultrasonic speed" of a material is the speed of sound within the material at sound frequencies between one and ten MHz.

A primary object of the invention is to provide an ultrasound phantom useful in evaluating the ability of ultrasound medical diagnostic scanners to resolve objects of selected sizes located at various distances from the ultrasound scanning heads of the ultrasound scanners.

A second object of the invention is to provide such an ultrasound phantom having scatter and absorption characteristics resembling human soft tissue, such as breast or liver tissue.

Other objects, features, and advantages of the invention will be apparent from the following detailed description taken in conjunction with the accompanying drawings.

DETAILED DESCRIPTION OF THE PREFERRED EMBODIMENT

Figure 1:
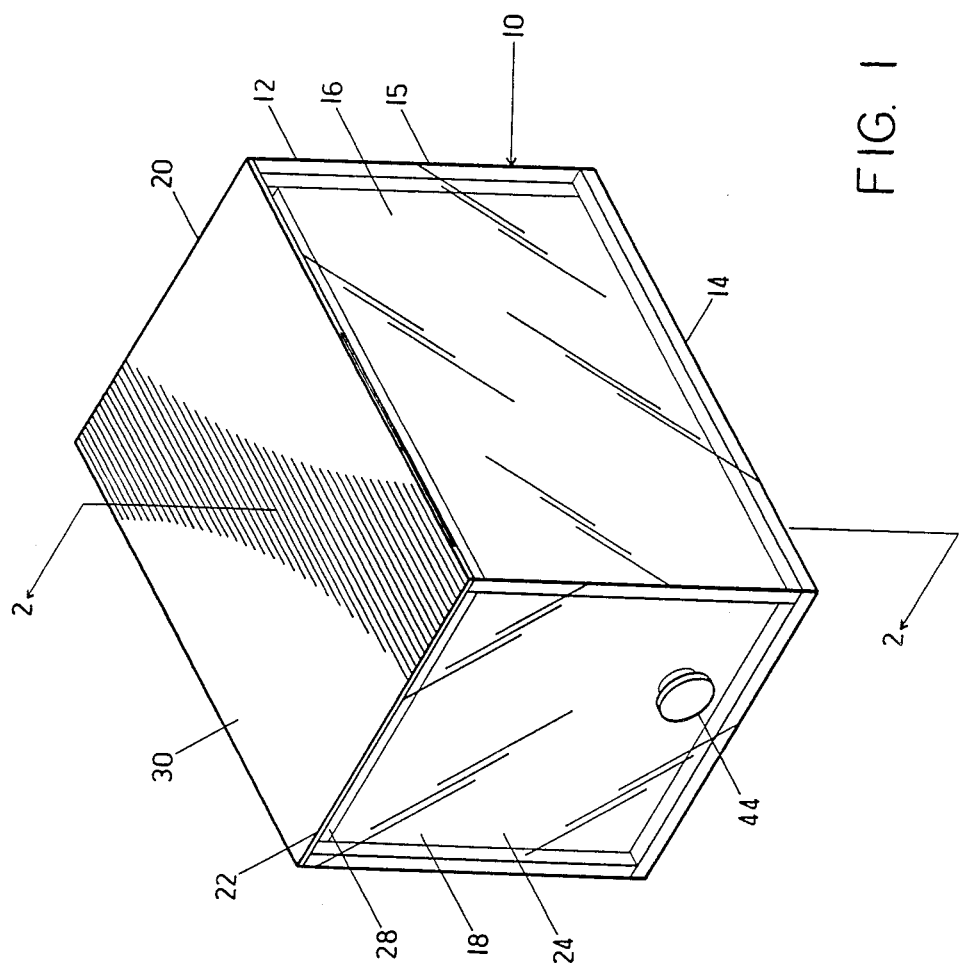
FIG. 1 is a perspective view of a phantom made in accord with the invention, showing the top, front, and one side surface of the phantom.

Referring more particularly to the drawings, wherein like numbers refer to like parts, FIG. 1 shows a first embodiment of an ultrasound phantom, generally indicated at 10, constructed in accord with the present invention. The ultrasound phantom 10 includes a container 12 having a bottom 14 and walls 15. Preferably the walls 15 include opposed faces 16, and opposed ends 18. Taken together, the bottom, faces, and ends 14, 16, and 18 form a hollow, box-like structure. Margins of the walls 15 remote from the bottom 14 define a window 20. The window 20 is closed with an ultrasound-transmitting window cover 22. The window cover 22 may be made of any cohesive ultrasound transmitting material of suitable physical durability. A thin sheet of polyurethane or saran is preferred.

The ultrasound phantom 10 further includes a phantom body 24. The phantom body substantially fills the container 12 up to the level of the window 20, except as shall be discussed below. The phantom body 24 includes a matrix 26 made of a matrix material exhibiting ultrasound characteristics that mimic animal soft tissue. A matrix material (or any other material forming a part of the phantom 10) shall be deemed to mimic animal soft tissue if, when compared to the corresponding ultrasound characteristics of the animal soft tissue, its attenuation coefficient differs by no more than 10%, its ultrasonic speed by 1%, its specific gravity by 10%, and its backscatter coefficient is within the same order of magnitude.

At least in theory, the more exactly these characteristics of the tissue mimicking material correspond to those of the animal soft tissue, the more precisely will results obtained by ultrasound scanning of the phantom allow the user of the phantom to predict the scanning characteristics of the same equipment when used on animal soft tissue. A suitable and preferred matrix material for the matrix 26 is an agar gel containing four and one half weight percent agar in water, with selected solid particles (not shown) dispersed throughout the agar to adjust the attenuation and scatter coefficients thereof. To adjust the attenuation coefficient, the solid particles include among them attenuation particles having a diameter not in excess of 40 microns and in any event insufficiently large to cause detectable backscatter. In practice, graphite particles having a diameter not in excess of 22 microns have been found suitable. A detergent may be mixed with the agar, if necessary, in amounts sufficient to prevent clumping of the graphite particles.

The solid particles also include scattering particles having a diameter such that their presence increases the backscatter coefficient of the matrix material. To be effective, a scattering particle must be large enough so that measurable ultrasonic scatter occurs and small enough and sufficiently closely spaced that the texture pattern displayed by the ultrasound scanner being tested does not represent resolution of individual scattering particles. Any material that differs from the agar in specific gravity and/or ultrasonic speed is capable of causing scatter. Glass beads have been found acceptable for use as scattering particles, with the diameter of the glass beads being not less than forty microns and not greater than one hundred microns. With the attenuation particles present in a concentration of 50 gms of graphite per liter and scattering particles in a concentration of ten glass beads per cubic millimeter (mean diameter of 84 microns), a matrix 26 made of such tissue mimicking matrix material and held at 22° C. has a specific gravity of 1.04 gm/cm$^3$, a ultrasonic speed of 1540 m/s, an attenuation coefficient 1.10 dB/cm at 2 MHz (corresponding to a rate of change of a attenuation coefficient with frequency of 0.55 dB/cm/MHz), and an estimated backscatter coefficient of $3 \times 10^{-3}$ cm$^{-1}$ sr$^{-1}$ at 3.0 MHz. A matrix 26 composed of such material is a good mimicker of solid organ tissue such as liver and breast tissue.

The preferred matrix material just described contains water and is subject to drying by escape of the water to the atmosphere. This results in changes in acoustic properties that make the matrix material a less effective tissue mimicker. Consequently, when such a matrix material is used, the container 12 must be liquid tight and preferably also water vapor tight. The window cover 22 must include means for reducing water transfer therethrough. To this end, the window cover 22 may be made of a flexible plastic material that does not readily transmit water vapor. An alternative means for reducing water transfer through the window cover 22 includes a layer 28 of an oil-based gel that completely closes the window 20, adhering to the uppermost portions of the faces 16 and ends 18 in water and water vapor-tight relation. The layer 28 of oil-based gel preferably is also covered with a thin and flexible plastic sheet 30 that serves to form and protect the surface of the layer 28 of oil-based gel.

In practice, the bottom 14, faces 16, and ends 18 may be molded as a unit or formed of flat pieces of plastic or other material and be glued or otherwise joined so as to constitute the container 12. If the window cover 22 is to include the layer of oil-based gel, the plastic sheet 30 may first be glued or otherwise attached to the container 12 so as to close the window 20 in liquid-tight relation. At least one of the bottom 14, faces 16, or ends 18 includes a filling hole, shown at 32 and located in an end 18 of the ultrasound phantom 10 shown in FIGS. 1-3. The layer 28 of oil-based gel may then be created by inserting through the filling hole 32 a sufficient quantity of the oil-based gel to make the layer 28, the oil-based gel so inserted being in molten form. With the container 12 oriented so that the window 20 is downwardmost, the molten oil-based gel may then be allowed to cool and solidify. The exact thickness of the layer 28 is not critical.

After the layer 28 of oil-based gel has been formed, the remainder of the container 12 may be filled with the matrix material selected to form the matrix 26 by inserting the matrix material in molten form through the filling hole 32 and allowing it subsequently to solidify. It is important that the matrix 26 completely fill the space remaining in the container 12 beneath the level of the layer 28 of oil-based gel, with no air bubbles remaining. Any of a number of convenient techniques may be utilized to accomplish this end. It is convenient to utilize a filling syringe, shown in cross section in FIG. 3 at 34. The filling syringe 34 may be any conventional syringe with a barrel 36, plunger 38, and plunger seal 40. The portion of the barrel 36 that would normally be adapted to receive a needle may be cut off to leave the barrel open-ended. The filling syringe 34 is selected to have a size sufficiently large that the barrel 36 may be attached to the end 18 in which the filling hole 32 is located, with the barrel entirely surrounding and thus closing the filling hole 32.

When the matrix material selected to form the matrix 26 is inserted through the filling hole 32, as described above, it is inserted through the barrel 36 of the filling syringe 34, with the plunger 38 removed. The matrix material is allowed also to fill part of the barrel 36. With the matrix material still in its molten form, the plunger 38 is reinserted into the barrel 36 with a strand of wire, such as that shown in FIG. 3 at 42, inserted beside the plunger 38 to extend past the plunger seal 40 into the barrel 36. The wire 42 distorts the plunger seal 40 sufficiently that air bubbles and any excess molten matrix material may escape past the plunger seal 40. The filled container 12 may be manually rotated and shaken so as to direct all air bubbles contained therein up into the barrel 36 of the filling syringe 34 and further up against the plunger seal 40 near the position of the wire 42. By application of pressure to the plunger 38, any such air bubbles may be forced past the plunger seal 40 at the point where the wire 42 has distorted the plunger seal. By this means, the container 12 may be entirely filled, with all air bubbles removed. The wire 42 may then be pulled out of the barrel 36 from the plunger 38 side, whereupon the plunger seal 40 prevents the readmission of any air to the container 12.

Typically the material of which the matrix 26 is made contains scattering particles, as discussed above, having a different specific gravity than the remainder of the matrix material. For example, the preferred matrix material disclosed above utilizes glass beads as scattering particles and suspends them within agar. The glass beads so described have a higher specific gravity than the agar and, unless otherwise provided for, they would tend to sink within the matrix material until the gel had solidified. To avoid this result and to maintain the scattering particles in a uniform distribution throughout the matrix 26, a slight pressure is maintained on the plunger 38 by application of rubber bands or the like, and the entire ultrasound phantom 10 is rotated about a horizontal axis until the gel of the matrix 26 has solidified. A rotation rate of approximately 2 RPM has been found to be sufficient. After the material forming the matrix 26 has solidified, the filling syringe 34 may be removed from the container 12 and the filling hole 32 closed by any convenient means, such as the stopper shown in FIG. 2 at 44.

The phantom body 24 contains, in addition to the matrix 26, testing spheres 46. Preferably, the testing spheres 46 are made of a material having the same specific gravity, ultrasonic speed, and attenuation coefficient as the material of the matrix 26. However, the testing spheres 46 are made of a material having a backscatter coefficient different from that of the matrix 26. When the preferred matrix material described above is used for making the matrix 26, the testing spheres 46 may most conveniently be made of the same agar gel with the same attenuation particles as those incorporated into the matrix. However, a different concentration of scattering particles is used. An extreme difference in scattering coefficient is attained when no backscattering particles are used in the testing spheres 46.

When agar is used in the material selected to make the testing spheres 46, the agar may be made up in molten form, with attenuation particles and scattering particles (if any) mixed therein. The testing spheres 46 may be conveniently molded in a two part, split mold of conventional design (not shown). If necessary in order to distribute any attenuation or scattering particles uniformly through the testing spheres 46, the filled mold may be rotated as the testing spheres solidify. Because the melting point of agar is approximately 78° C. and the congealing point is approximately 38° C., agar testing spheres 46 may be made first and then be mixed with a molten agar based matrix material held at a temperature less then 78° C. and greater then 38° C. The testing spheres 46 be mixed with the matrix material prior to the filling of the container 12. With the container filled, it is recommended that it be vigorously shaken and agitated with a rotational motion prior to rotation at 2 RPM. This is to assure a random distribution of the testing spheres before the matrix begins to solidify. When the matrix 26 has solidified, the testing spheres 46 are embedded within it, distributed throughout the phantom body 24 in a random array or at least in unpredictable locations therein.

Figure 2:
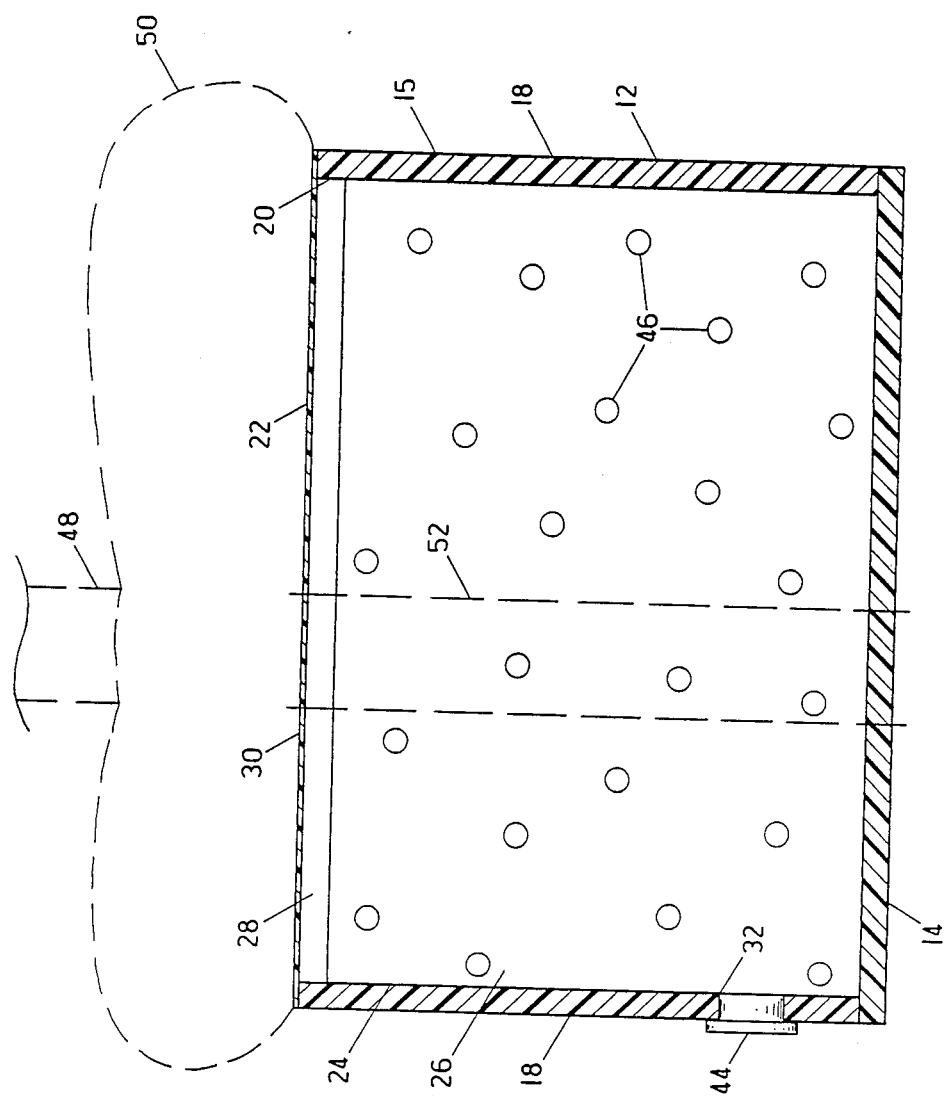
FIG. 2 is a cross sectional view of the phantom of FIG. 1 taken along section line 2—2, with a ultrasound scanning head and water bag shown drawn with broken lines. The testing spheres of the phantom body are not shown to scale or in numbers accurately reflecting their concentration within the phantom body.
Figure 3:
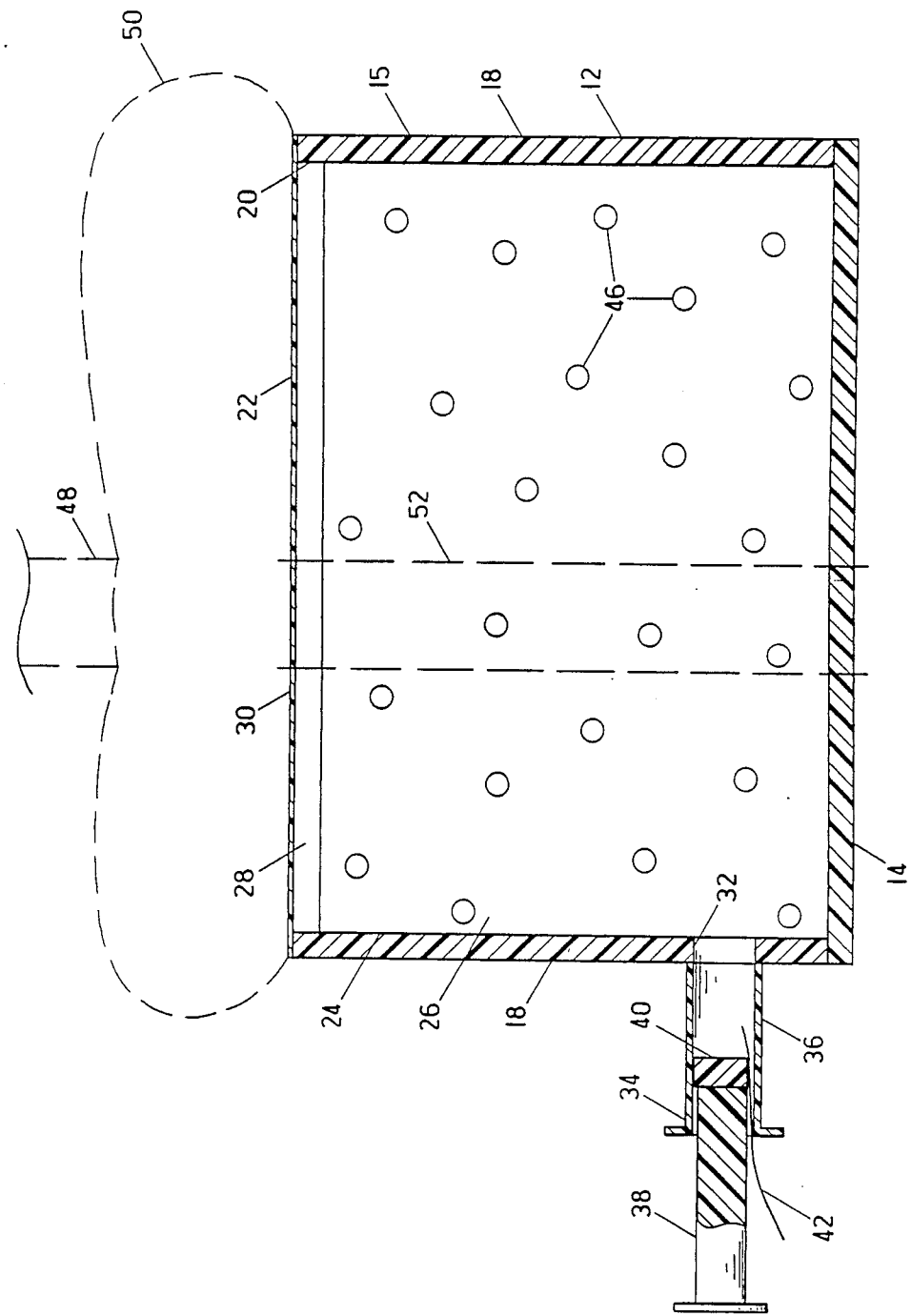
FIG. 3 is a cross sectional view of the phantom of FIG. 1 comparable to the view of FIG. 2 except that a filling syringe is shown attached to the container of the phantom.

The diameter of the testing spheres 46 is selected to be of a size appropriate for testing the resolution abilities of an ultrasound scanner having a ultrasound scanning head, such as that shown in phantom in FIG. 2 at 48. The ultrasound scanning head 48 may either be directly applied to the window cover 22 or, as is shown in FIG. 2, may be equipped with a water bag 50 or any of the other spacers or surface conformation arrangements commonly used with diagnostic and other ultrasound ultrasound scanning heads. As is well known to those skilled in the art, an ultrasound scanning head may be used to scan a space below it commonly referred to as a slice, indicated in phantom in FIG. 2 at 52. Any ultrasound scanning head has a zone within the slice being scanned within which it achieves resolution of objects of a given size and acoustical characteristics. This zone will be referred to herein as the ultrasound scanning head's "resolution zone." No matter what size of testing sphere 46 is employed, it will be apparent that the phantom 10 may be used to demonstrate the ability of the ultrasound scanning head 48 to resolve spheres of that size at any given location within the slice 52. Furthermore, the phantom 10 can be used to demonstrate the ability of the ultrasound scanner to so detect the testing spheres 46 when they differ from the matrix 26 in backscatter coefficient or other ultrasound acoustical property to any selected extent.

When resolution characteristics are being tested with the phantom, user bias is always a potential source of inaccuracy. If one knows where an object to be resolved is located, it is easy to convince oneself that the object is being seen there. It will be apparent that the unpredictable location of the testing spheres 46 within the phantom body 24 virtually eliminates the possibility of such user bias. This is an important and advantageous feature.

Figure 4:
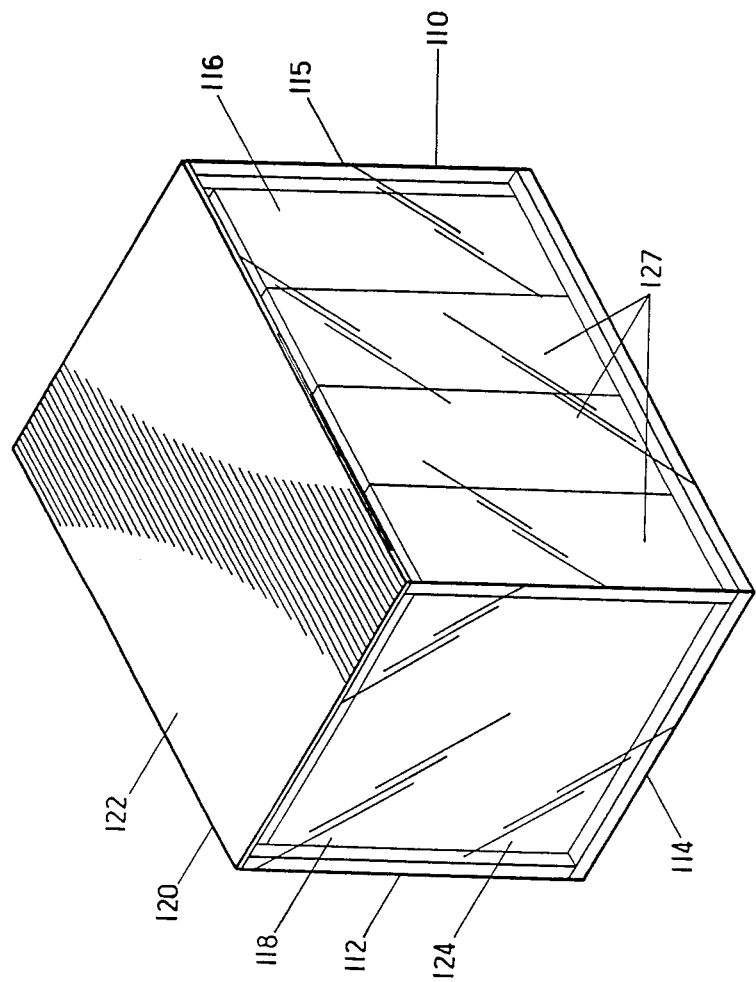
FIG. 4 is a perspective view corresponding to FIG. 1 of a second embodiment of a phantom made in accord with the invention.

The ultrasound phantom 10 is designed to be used to determine the limits of performance of ultrasound scanners to be tested. Typically the resolution zone varies with ultrasound wave length and energy, the shape of the ultrasound beam, the size of the objects to be detected (larger objects being easier to resolve than smaller ones) and the magnitudes of difference in acoustical characteristics between the objects to be resolved and the material surrounding them. Consequently, an especially useful embodiment of the ultrasound phantom of the invention is the alternative embodiment shown in FIG. 4 at 110.

The alternative embodiment of the phantom 110 includes a container 112 having a bottom 114, walls 115 preferably including faces 116 and ends 118, window 120, window cover 122, and phantom body 124, all corresponding in structure to the similarly named parts of the first embodiment discussed above. However, the phantom body 124 is divided into generally rectangular, box-shaped subsections 127. Each subsection 127 extends between the opposing faces 116. Within each subsection, the phantom body 124 includes a matrix corresponding in structure to the matrix 26 of the first embodiment, discussed above. Furthermore, the phantom body 124 includes testing spheres, corresponding to the testing spheres 46 of the first embodiment. All of the testing spheres within a given subsection 127 have the same size, ultrasonic speed, attenuation coefficient and backscatter coefficient. Preferably a first subsection 127 has no testing spheres whatsoever. Subsequent subsections 127 contain spheres that are at first difficult and then are increasingly easy to resolve with the ultrasound scanner being tested. Thus, one subsection 127 may have testing spheres of a size so small that resolution is impossible, while subsequent subsections may have spheres of increasing sizes until the testing spheres are large enough that resolution is not difficult. Alternatively, ultrasonic speeds, specific gravities, attenuation coefficients, and backscatter coefficients may be allowed to vary in the testing spheres of successive subsections 127.

Described generally, the alternative embodiment of the phantom 110 may be an ultrasound phantom wherein the phantom body 124 is divided into a plurality of subsections 127, each including a matrix, all of the matrices being made of a single matrix material, and wherein the testing spheres of a first subsection differ in backscatter coefficient from the testing spheres of the remaining subsections. The ultrasound phantom 110 may alternatively be described as an ultrasound phantom in which the phantom body 124 includes a plurality of subsections 127, each of which includes a matrix made of matrix material indistinguishable by an ultrasound scanner to be tested from the matrix materials of the remaining subsections. A first subsection 127 has testing spheres having a first size, ultrasonic speed, specific gravity, attenuation coefficient, and backscatter coefficient, and at least a second subsection has testing spheres having a second size, ultrasonic speed, specific gravity, attenuation coefficient, and backscatter coefficient, the first and second sizes, ultrasonic speeds, specific gravities, attenuation coefficients, and backscatter coefficients being so different from each other that the susceptibility of the testing spheres of the first and second subsections to resolution by the ultrasound scanner differs.

The alternative embodiment of the phantom 110 may be made by casting each subsection 127 separately in the manner that the phantom body 24 of the first embodiment 10 was made, as described above. The subsections 127 may then be joined, with or without additional gel to glue them together, within the container 112. With the bottom 114 removed, the window cover 122 may be fastened in place over the window 120, the subsections 127 introduced through the open bottom of the container 112, and the bottom 114 finally fastened in place to complete the container.

In use, the ultrasound scanning head of the ultrasound scanner to be tested is placed in contact with the window 120 of the phantom 110. Contact may be direct or it may be indirect by the employment of water bags, stand off pads, and other means well known to those skilled in the art. The ultrasound scanning head is then allowed to scan each of the subsections 127 either successively or with the slice extending through more than one subsecton 127 at a time. The subsection 127 without spheres serves as a control. As the spheres become increasingly easier to resolve, the ultrasound scanning head eventually will resolve them. As the testing spheres become even more easily resolved, the zone within the phantom 110 in which they can be resolved will for many ultrasound scanners be observed to increase. Thus, the phantom 110 provides a convenient means to find out how small a testing sphere can be resolved over a given range of distances from the ultrasound scanning head (or how slight a difference in backscatter coefficient or some comparable acoustic characteristic can be detected).

Although the embodiments of the invention disclosed above are those preferred, it will be apparent that certain alterations and adaptations may be made to produce equivalent phantoms using other materials, arrangements, and modes of assembly. Therefore, it is understood that the present invention is not limited to the particular construction and arrangement of parts illustrated and disclosed above. Instead, it embraces all such modified forms thereof as come within the scope of the following claims.

What is claimed is:

1. An ultrasound phantom for use with an ultrasound scanner comprising:
   (a) a container having a bottom and walls, margins of the walls remote from the bottom defining a window, which is closed by an ultrasound-transmitting window cover; and
   (b) a phantom body contained within the container and including a matrix made of a matrix material exhibiting a matrix ultrasonic speed, specific gravity, attenuation coefficient, and backscatter coefficient, the phantom body further including scattering particles small enough and spaced sufficiently close to each other that the scanner is incapable of resolving individual scattering particles and a multiplicity of testing spheres having a testing sphere ultrasonic speed, specific gravity, attenuation coefficient, and backscatter coefficient, at least one of which is different from the corresponding matrix ultrasonic speed, specific gravity, attenuation coefficient, and backscatter coefficient, the testing spheres being located within the phantom body in a random and unpredictable array and at least some of the testing spheres being of a size, spaced sufficiently far apart, and having acoustical characteristics such that the ultrasound scanner is anticipated to be able to resolve them individually embedded in the matrix material.

2. The ultrasound phantom of claim 1 wherein the matrix and testing sphere ultrasonic speeds, specific gravities, and attenuation coefficients are substantially the same and the matrix and testing sphere backscatter coefficients are sufficiently different as to render testing spheres of a size sufficient to be resolved by the ultrasound scanner distinguishable within the matrix.

3. The ultrasound phantom of claim 1 wherein the phantom body is divided into subsections, each including a matrix, all of the matrices being made of a single matrix material, and wherein the size of the testing spheres is uniform within a subsection but differs from subsection to subsection.

4. The ultrasound phantom of claim 1 wherein the phantom body is divided into subsections, each including a matrix, all of the matrices being made of a single matrix material, and wherein the testing spheres of a first subsection differ in backscatter coefficient from the testing spheres of the remaining subsections.

5. The ultrasound phantom of claim 1, the phantom body of which phantom includes subsections each of which includes a matrix made of a matrix material and indistinguishable by the ultrasound scanner from the matrix materials of the remaining subsections, a first subsection having testing spheres having a first size, ultrasonic speed, specific gravity, attenuation coefficient, and backscatter coefficient, and at least a second subsection having testing spheres having a second size, ultrasonic speed, specific gravity, attenuation coefficient, and backscatter coefficient, the first and second sizes, ultrasonic speeds, specific gravities, attenuation coefficients, and backscatter coefficients being so different from each other that the susceptibility of the testing spheres of the first and second subsections to resolution by the ultrasound scanner differs.

6. The ultrasound phantom of claim 5 wherein the first and second ultrasonic speeds, specific gravities, attenuation coefficients, and backscatter coefficients are sufficiently similar that the ultrasound scanner is unable to distinguish between them, and the testing spheres of the first and second subsections differ only in size.

7. The ultrasound phantom of claim 5 wherein the first and second sizes, ultrasonic speeds, specific gravities, and attenuation coefficients are indistinguishable by the ultrasound scanner, and the testing spheres of the first and second subsections differ only in backscatter coefficients.

8. The ultrasound phantom of claim 5 including a subsection having testing spheres none of which are susceptible to being resolved by the ultrasound scanner and an additional subsection having testing spheres that may be readily resolved by the ultrasound scanner.

9. The ultrasound phantom of claim 5 including a subsection having no testing spheres.

* * * * *

UNITED STATES PATENT AND TRADEMARK OFFICE
CERTIFICATE OF CORRECTION

PATENT NO. : 4,843,866

DATED : July 4, 1989

INVENTOR(S) : Madsen et al.

It is certified that error appears in the above-identified patent and that said Letters Patent is hereby corrected as shown below:

Column 1, line 1 insert as first paragraph.

--This invention was made with United States Government support under NIH Grant numbers R01 CA25634 and R01 CA39224, awarded by the Department of Health and Human Services. The United States Government has certain rights to this invention.--

Signed and Sealed this

Twenty-fourth Day of April, 1990

Attest:

HARRY F. MANBECK, JR.

Attesting Officer

Commissioner of Patents and Trademarks